United States Patent [19]

Pluss et al.

[11] 4,150,232

[45] Apr. 17, 1979

[54] 1-CARBOXYMETHYL-3-SULFOLOWERAL-KYL PYRIDINIUM BETAINE INNER SALTS

[75] Inventors: Kurt Pluss; Bruno R. De Martin, both of Schaffhausen, Switzerland

[73] Assignee: Cilag-Chemie A.G., Schaffhausen, Switzerland

[21] Appl. No.: 916,014

[22] Filed: Jun. 15, 1978

Related U.S. Application Data

[60] Division of Ser. No. 816,104, Jul. 15, 1977, which is a division of Ser. No. 763,452, Jan. 27, 1977, Pat. No. 4,067,785, which is a continuation-in-part of Ser. No. 666,525, Mar. 12, 1976, abandoned.

[51] Int. Cl.$^2$ ............................................ C07D 213/71
[52] U.S. Cl. ........................................ 546/339; 204/49
[58] Field of Search ................................... 260/294.85

[56] References Cited

U.S. PATENT DOCUMENTS

| | | | |
|---|---|---|---|
| 3,444,056 | 5/1969 | Richter et al. | 204/49 |
| 3,862,019 | 1/1975 | Rosenberg et al. | 204/49 |

*Primary Examiner*—Alan L. Rotman
*Attorney, Agent, or Firm*—Salvatore R. Conte

[57] ABSTRACT

Novel pyridyl alkyl sulfonic acid betaines useful as additives to nickel electroplating baths.

4 Claims, No Drawings

1-CARBOXYMETHYL-3-SULFOLOWERALKYL PYRIDINIUM BETAINE INNER SALTS

CROSS-REFERENCE TO RELATED APPLICATION

This is a division of application Ser.No. 816,104, filed July 15, 1977 which in turn is a division of Ser. No. 763,452, filed Jan. 27, 1977, now U.S. Pat. No. 4,067,785 issued Jan. 10, 1978 which in turn is a continuation-in-part of Ser. No. 666,525, filed Mar. 12, 1976 now abandoned.

BACKGROUND OF THE INVENTION

Pyridyl sulfonic acids or pyridyl alkyl sulfonic acids as additives to nickel plating baths have been reported. In U.S. Pat. No. 2,839,456, 4-pyridyl ethane sulfonic acid, in combination with other additives, is described as a brightener. Though 2- and 4-pyridine ethane sulfonic acids do improve the luster of deposited nickel layers, they have no influence on their leveling. In U.S. Pat. No. 3,444,056, certain quaternary compounds of pyridine-3-sulfonic acid are mentioned as levelers and brighteners. The N-methyl-pyridine-3-sulfonic acid betaine and N-allyl-pyridine-3-sulfonic acid betaine mentioned in this patent are, however, not fully satisfactory. It appears that nickel deposits turn lusterless and brittle with a too low ampere hour load per liter of nickel bath. This behavior of the bath cannot be prevented by any of the regeneration methods employed in electroplating. The instant compounds of this invention are agents which produce a highly leveled nickel deposit of excellent ductility in a far more constant bath.

DESCRIPTION OF THE PREFERRED EMBODIMENTS

This invention relates to a novel class of pyridyl alkyl sulfonic acid betaines represented by the following formula:

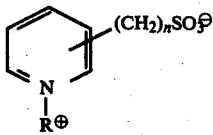

in which the substituent $-(CH_2)_nSO_3^\ominus$ is in the 2- or 4-position of the pyridyl ring; n is the integer 1 or 2; and R is a member selected from the group consisting of methyl; methallyl; $CH_2COOH$; $CH_2(CH_2)_xCH_2SO_3Na$ wherein x is the integer 1 or 2; sodium 2-hydroxypropylsulfonate; sodium 2-hydroxybutylsulfonate; sodium 3-hydroxybutylsulfonate; benzyl, halobenzyl; loweralkylbenzyl; and benzyl substituted with the group:

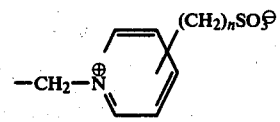

wherein the substituent $-(CH_2)_nSO_3^\ominus$ is in the 2- or 4-position of the pyridyl ring and n is the integer 1 or 2.

For purposes of nomenclature, the aforementioned groups: sodium 2-hydroxypropylsulfonate; sodium 2-hydroxybutylsulfonate and sodium 3-hydroxybutylsulfonate may also be denoted as 3-Na-sulfo-2hydroxypropyl, 4-Na-sulfo-2-hydroxybutyl and 4-Na-sulfo-3-hydroxybutyl, respectively. Similarly, the aforementioned group: $CH_2(CH_2)_xCH_2SO_3Na$ may be denoted as 3-Na-sulfopropyl when x=1, and 4-Na-sulfobutyl when x=2.

As used herein, the term "loweralkyl" refers to an aliphatic hydrocarbon with 1 to 4 carbons; and the term "halo" includes bromo and fluoro, with chloro preferred, that is, those halogens with atomic weight less than 80.

The subject pyridyl alkyl sulfonic acid betaines (I) are conveniently prepared by quaternization of an appropriate 2- or 4-pyridyl alkyl sulfonic acid (II-a) or its alkali metal salt, preferably the sodium salt (II-b):

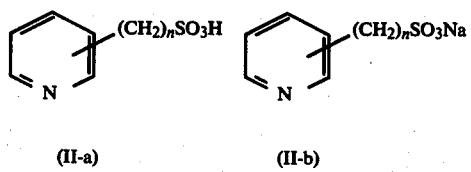

wherein the substituent $-(CH_2)_nSO_3(H,Na)$ is in the 2- or 4-position of the pyridyl ring and n is 1 or 2. Quaternization is accomplished by using an appropriate quaternizing agent suitable for introducing the aforementioned R-substituent on the ring nitrogen of the pyridyl function, such as, for example, dimethyl sulfate, methallyl chloride, sodium chloroacetate, propansultone, butansultone, an appropriate benzyl halide, an appropriately substituted haloloweralkyl, and the like agents, as more fully described and exemplified hereinafter. The compounds of formulas (II-a) and (II-b) are obtained from known procedures in the art, for example, by reaction between 2- or 4-vinylpyridine and sodium bisulfite according to J. Am. Chem. Soc., 69, 2465 (1947) for the preparation of the ethyl sulfonic acids or by reaction between appropriate haloalkyl pyridines and sodium sulfite.

To prepare the formula (I) compounds with R equal to methyl, the precursor (II-a) or (II-b) is reacted with dimethyl sulfate as the quaternizing agent, generally utilizing a slight stoichiometric excess of the latter. Elevated temperatures may be employed to enhance the rate of reaction. Since dimethyl sulfate is a liquid at ambient temperatures, the use of an additional organic solvent for the quaternization reaction is normally unnecessary. The reaction may be illustrated as follows:

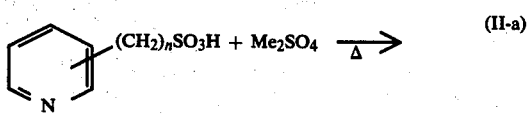

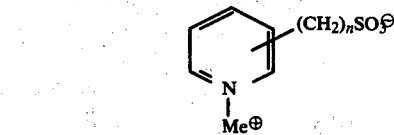

To prepare the formula (I) compounds with R equal to $CH_2COOH$, approximately equimolar amounts of the precursor (II-b) and haloacetic acid in the form of an alkali metal salt, for example, sodium (III) in an aqueous solvent are reacted, preferably under reflux conditions. The reaction mixture containing the thus-formed alkali metal salt is then cooled and treated with a suitable mineral acid, e.g., hydrochloric acid, to convert the salt (IV) to its corresponding acid form (V). The foregoing reaction may be illustrated as follows:

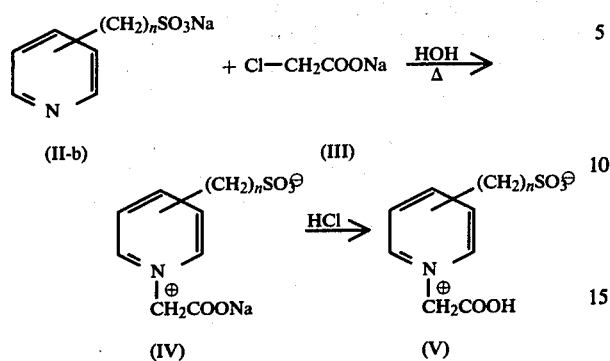

The compounds of formula (I) wherein R is benzyl, halobenzyl or loweralkylbenzyl are prepared in similar fashion. The precursor (II-b) is reacted with an appropriate benzyl halide (VI), e.g., benzyl chloride, halobenzyl chloride or loweralkybenzyl chloride, in water, preferably under reflux conditions. After cooling and treatment with mineral acid, the desired N-benzyl substituted product (VII) is obtained.

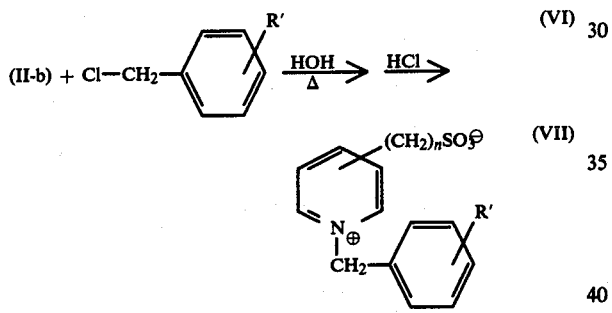

R' = H, halo, loweralkyl

The compounds of formula (I) wherein R is methylallyl may be similarly quaternized, as described above for R equal to a benzyl function, except that methallyl chloride is used as the quaternizing agent.

The compounds of formula (I) wherein R is $CH_2(CH_2)_xSO_3Na$ may be prepared by quaternization of the precursor (II-b) with propansultone or butansultone, respectively (VIII), in an aqueous solvent. Elevated temperatures may be employed to enhance the rate of reaction. Treatment of the reaction mixture with mineral acid, preferably after volume concentration, is employed to counteract the sodium ion content followed by conventional treatment with suitable bases yielding sodium anion, e.g., sodium methylate in methanol to yield the desired sodium alkylsulfonate derivative (IX). In like manner, the compounds of formula (I) wherein R is sodium 2-hydroxypropylsulfonate, sodium 2-hydroxybutylsulfonate or sodium 3-hydroxybutylsulfonate are obtained by quaternizing (II-b) with an appropriate halo-hydroxyalkyl sulfonic acid in sodium salt form, as illustrated below by sodium 2-hydroxypropylsulfonate (X).

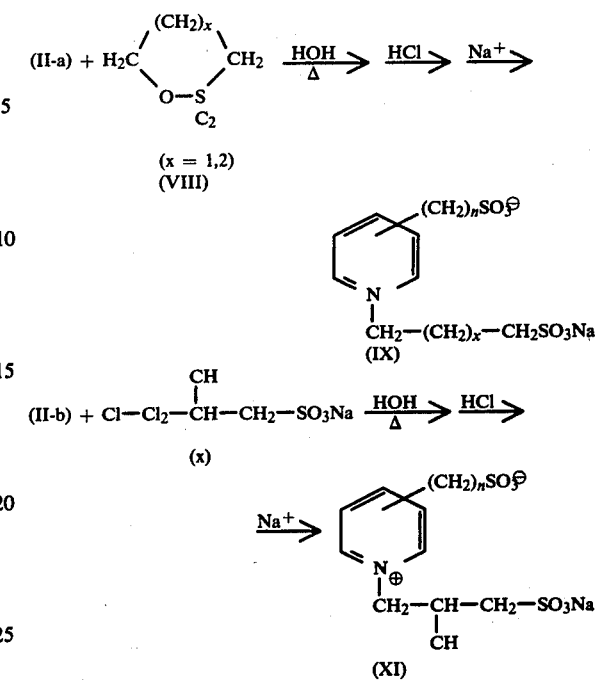

To prepare the compounds of formula (I) wherein R is benzyl substituted with the group:

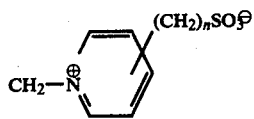

α,α'-dichloroxylol (o-, m- or p-form) is reacted with at least two stoichiometric equivalents of the precursor (II-b) in an aqueous solvent. Elevated temperatures are advantageously employed to enhance the rate of reaction. Upon completion of the reaction and subsequent cooling of the reaction mixture, followed by treatment with mineral acid, the desired products are obtained through conventional recovery techniques. The foregoing quaternization can be illustrated with α,α'-dichloro-p-xylol as follows:

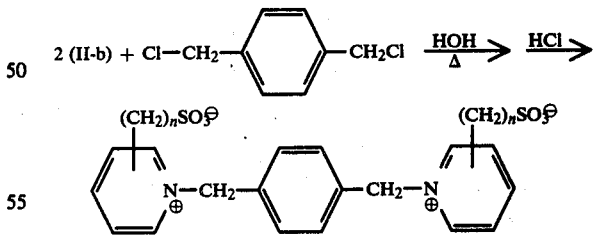

The subject compounds of formula (I) produce a highly leveled nickel deposit of excellent ductility when used as additives for the electro-deposition of nickel coatings in conventional galvanic nickel baths. These compounds are suitable for use in galvanic nickel baths either alone or in combination with other luster-promoting or leveling additives. For example, an optimum luster is obtained in combination with such generally known brighteners as saccharin, diarylsulfonimides naphthalene trisulfonic acids or sulfonates, acetylenic compounds such as, for example, propargyl alcohol, and the like. The latter is especially useful in enhancing the leveling effect of the subject compounds. Furthermore, the subject compounds may be used in conjunction with conventional wetting agents such as, for example, sodium lauryl sulfate or with other ionized or non-ionized agents that decrease surface tension. The galvanic baths may also contain conventional buffering agents, such as, for example, boric acid, tartrates, etc.

The galvanic bath comprises an acidic solution of a nickel salt generally one selected from the group consisting of nickel sulfate, nickel sulfamate, nickel fluoborate, nickel chloride, nickel acetate and the like. Mixtures of such salts are also suitable. Typical of the nickel galvanic baths in which the subject compounds (I) may be employed are those shown in U.S. Pat. No. 3,444,056. The subject compounds may be advantageously used in concentrations ranging from about 0.05 gram per liter (g/l) to about 2.0 g/l of bath, although from about 0.1 to about 0.5 g/l is preferred. Other preferred parameters are a bath temperature of about 50°–60° C., a pH of about 3.5–5.0 with about 4.5 most preferred, and a current density ranging from about 1 to about 10 amp/dm². The bath may be mechanically or air stirred. If the latter, the use of a non-foamy wetting agent is recommended.

In view of the foregoing, the present invention provides an improvement in galvanic baths for electrodepositing leveled and lustrous nickel comprising an aqueous acidic solution of at least one nickel salt. The improvement in such baths comprises a pyridyl alkyl sulfonic acid betaine of formula (I) in a concentration of about 0.05–2.0 grams per liter and, preferably, about 0.1–0.5 grams per liter. The preferred additives of formula (i) are those wherein R is either benzyl or benzyl substituted with the previously described group:

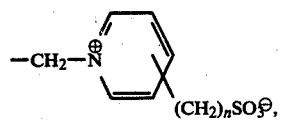

including but not limited to 2-[N-benzylpyridyl-(2)]-ethane sulfonic acid betaine and 1,2-bis-[2-(2-sulfoethyl)-pyridinium-(1)-methyl]-benzene.

The following examples are intended to illustrate, but not to limit, the scope of the present invention.

EXAMPLE I

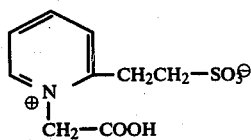

A. 2-[N-carboxymethyl-pyridyl-(2)]-ethanesulfonic acid betaine:

23.3 Grams (0.2 mol) of chloroacetic acid sodium salt, 41.8 g (0.2 mol) of 2-pyridyl ethane sulfonic acid sodium salt and 50 g of water are refluxed for five hours. Following cooling down to 20° C., the reaction mixture is treated with 250 g of concentrated hydrochloric acid. The crystallized sodium chloride is filtered off by suction and the solution is concentrated to dryness under vacuum. The residue is mixed with 350 ml of methanol. The product, 27.5 g of 2-[N-carboxymethyl-pyridyl-(2)]-ethanesulfonic acid betaine, which crystallizes at room temperature is filtered off by suction and vacuum dried at 110° C.; decomposition point: 214° C.

B. 2-[N-carboxymethyl-pyridyl-(4)]-ethane sulfonic acid betaine is obtained in the same way, by employing an equivalent quantity each of 4-pyridyl ethane sulfonic acid sodium salt and chloroacetic acid sodium salt as reactants; decomposition point: 234° C.

C. [N-carboxymethyl-pyridyl-(4)]-methanesulfonic acid betaine is obtained in the same way, by employing an equivalent quantity each of 4-pyridyl methane sulfonic acid sodium salt and chloroacetic acid sodium salt as reactants; decomposition point: 290° C.

EXAMPLE II

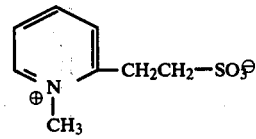

A. 2-[N-methyl-pyridyl-(2)]-ethane sulfonic acid betaine:

55 Grams (0.29 mol) of 2-pyridyl ethane sulfonic acid and 40.7 g (0.32 mol) of dimethyl sulfate are heated to 150°–155° C. Two hours later the reaction mixture is allowed to cool down to 20° C. and a mixture of 40 ml of ethanol and 40 ml of isopropanol are added. After standing for 24 hours, the precipitated crude product is filtered off by suction. After double recrystallization from methanol, the white crystals are vacuum dried at 80° C. The final yield is 16.8 g of 2-[N-methyl-pyridyl-(2)]-ethane sulfonic acid betaine; decomposition point: 209° C.

B. 2-[N-methyl-pyridyl-(4)]-ethane sulfonic acid betaine is prepared in the same manner from equivalent amounts of 4-pyridyl ethane sulfonic acid and dimethyl sulfate.

EXAMPLE III

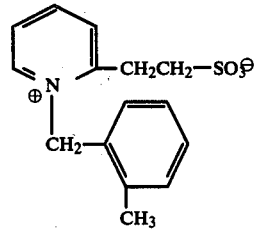

A. 2-[N-(2-methylbenzyl)-pyridyl-(2)]-ethane sulfonic acid betaine:

41.8 Grams (0.2 mol) of 2-pyridyl ethane sulfonic acid sodium salt, 28.1 g (0.2 mol) of o-methylbenzyl chloride and 20 g of water are refluxed for 5 hours. The reaction mixture is then allowed to cool down to 20° C. and 250 g of concentrated hydrochloric acid are added. The precipitated sodium chloride is filtered off by suction and the filtrate concentrated to dryness under vacuum. The residue is mixed with 200 ml of ethanol and the precipitated white crystal mass is filtered off by suction and vacuum dried at 110° C. to yield 32 g of 2-[N-(2-methylbenzyl)-pyridyl-(2)]-ethane sulfonic acid betaine; decomposition point: 223° C.

B. 2-[N-(2-methylbenzyl)-pyridyl-(4)]-ethane sulfonic acid betaine is obtained in the same way, by using an equivalent quantity each of 4-pyridyl ethane sulfonic acid sodium salt and o-methylbenzylchloride as reactants; decomposition point: 241° C.

EXAMPLE IV

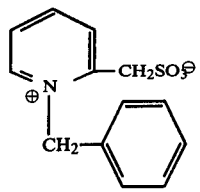

[N-benzyl-pyridyl-(2)]-methane sulfonic acid betaine:
17.3 Grams (0.1 mol) of 2-pyridyl methansulfonic acid sodium salt, 12.7 g (0.1 mol) of benzylchloride and 13 g of water are refluxed for 2 hours at 100°-105° C. The reaction mixture is allowed to cool down to 20° C. and 100 ml of concentrated hydrochloric acid are added. The precipitated sodium chloride is filtered off and the solution concentrated to dryness. The residue is mixed with 100 ml of ethanol. The precipitated white crystals are filtered off and vacuum dried at 110° C. to yield 13.7 g of [N-benzyl-pyridyl-(2)]methane sulfonic acid betaine; decomposition point: 230° C.

EXAMPLE V

By following the procedures of Examples III and IV, accept that equivalent quantities of appropriate reactants are employed, the following respective products are obtained:
  2-[N-benzylpyridyl-(2)]-ethane sulfonic acid betaine; decomposition point: 198° C.
  2-[N-benzylpyridyl-(4)]-ethane sulfonic acid betaine; decomposition point: 234° C.
  2-[N-(2-chlorobenzyl)-pyridyl-(2)]-ethane sulfonic acid betaine; decomposition point: 238° C.
  2-[N-(4-chlorobenzyl)-pyridyl-(2)]-ethane sulfonic acid betaine; decomposition point: 201° C.
  2-[N-(2-chlorobenzyl)-pyridyl-(4)]-ethane sulfonic acid betaine; decomposition point: 237° C.

EXAMPLE VI

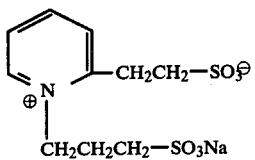

A. 2-[N-(3-Na-sulfopropyl)-pyridyl-(2)]-ethane sulfonic acid betaine:
41.8 Grams (0.2 mol) of 2-pyridyl ethane sulfonic acid sodium salt, 30.5 g (0.25 mol) of propansultone, 200 g of methanol and 15 g of water are heated to 65° C. for 7 hours. The reaction mixture is then concentrated under vacuum and the residue is mixed with 200 ml of concentrated hydrochloric acid. The precipitated sodium chloride is filtered off and the mother liquor concentrated to dryness. The oily residue is dissolved in 200 ml of methanol and allowed to stand for 2 days. Some 2-pyridyl ethane sulfonic acid, which precipitates within this time, is filtered off and the filtrate is neutralized with 30% sodium methylate solution (in methanol). A white salt precipitates which is filtered off and vacuum dried at 110° C. to yield 17 g of 2-[N-(3-Na-sulfopropyl)-pyridyl-(2)]-ethane sulfonic acid betaine; decomposition point: 228° C.

B. The procedure of Example VI-A is repeated except that an equivalent amount of butansultone is substituted for the propansultone used therein to yield the corresponding product, 2-[N-(4-Na-sulfobutyl)-pyridyl-(2)]-ethane sulfonic acid betaine.

C. By following the procedure of Example VI-A, except that equivalent amounts of appropriate starting materials are employed as reactants, there are obtained as respective products:
  [N-(3-Na-sulfopropyl)-pyridyl-(4)]-methane sulfonic acid betaine; and
  2-[N-(4-Na-sulfobutyl)-pyridyl-(4)]-ethane sulfonic acid betaine.

EXAMPLE VII

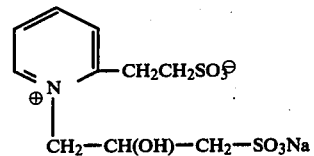

A. 2-[N-(3-Na-sulfo-2-hydroxypropyl)-pyridyl-(2)]-ethane sulfonic acid betaine:
20.9 Grams (0.1 mol) of 2-pyridyl ethane sulfonic acid sodium salt, 19.7 g (0.1 mol) of 3-chloro-2-hydroxypropyl sulfonic acid-(1)-sodium salt and 20 ml of water are heated at 95° C. for 6 hours. The reaction mixture is then concentrated under vacuum and the residue is mixed with 100 ml of concentrated hydrochloric acid. The insoluble sodium chloride is filtered off and the mother liquor concentrated to dryness. The oily residue is dissolved in 100 ml of methanol and allowed to stand for 2 days. Some 2-pyridyl ethane sulfonic acid, which precipitates within this time, is filtered off and the filtrate is neutralized with 30% sodium methylate solution (in methanol). The precipitated white salt is filtered off and vacuum dried at 110° C. to yield 11 g of 2-[n-(3-Na-sulfo-2-hydroxypropyl)-pyridyl-(2)]-ethane sulfonic acid betaine; decomposition point: 183° C.

B. The procedure of Example VII-A is followed, except that equivalent amounts of appropriate starting materials are employed as reactants, to yield the following respective products:
  2-[N-(4-Na-sulfo-2-hydroxybutyl)-pyridyl-(2)]-ethane sulfonic acid betaine;
  2-[N-(4-Na-sulfo-3-hydroxybutyl)-pyridyl-(4)]-ethane sulfonic acid betaine; and
  [N-(3-Na-sulfo-2-hydroxypropyl)-pyridyl-(4)]-methane sulfonic acid betaine.

EXAMPLE VIII

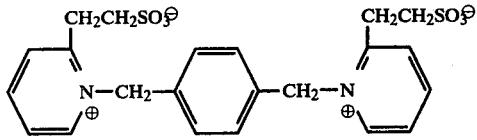

A. 1,4-Bis-[2-(2-sulfoethyl)-pyridinium-(1-methyl]-benzene:
62.8 Grams (0.3 mol) of 2-pyridyl ethane sulfonic acid sodium salt, 17.5 g (0.1 mol) of α,α'-dichloro-p-xylol and 50 g of water are heated to 100°-105° C. for 4 hours. The reaction mixture is then cooled and 200 g of concentrated hydrochloric acid are added. The precipitated sodium chloride is filtered off and, the filtrate concentrated under vacuum to dryness. 200 Ml of methanol are added to the residue. The precipitated impure crystals are filtered off, dissolved in 120 ml of water at 20° C., and again precipitated by adding 480 ml of ethanol. The white crystal mass is filtered off and vacuum dried at 110° C. to yield 26 g of 1,4-bis-[2-(2-sulfoethyl)-pyridinium-(1)-methyl]-benzene; decomposition point: >350° C.

B. In the same manner, except that equivalent amounts of appropriate reactants are employed, there are obtained as respective products:

1,2-bis-[2-(2-sulfoethyl)-pyridinium-(1)-methyl]-benzene; decomposition point: 248° C.

1,3-bis-[2-(2-sulfoethyl)-pyridinium-(1)-methyl]-benzene; decomposition point: 251° C.

1,4-bis-[4-(2-sulfoethyl)-pyridinium-(1-methyl]-benzene; decomposition point: 258° C.

EXAMPLE IX

The following illustrate typical galvanic nickel baths in which the subject compounds of formula (I) may be employed. It is understood that the hereinmentioned subject compounds are not listed for the purpose of limiting the scope of the invention thereto but to exemplify the usefulness of all compounds within formula (I).

| A | | |
|---|---|---|
| Nickel sulfate . 7H$_2$O | g/l | 310 |
| Nickel chloride . 6H$_2$O | g/l | 50 |
| Boric Acid | g/l | 40 |
| Lauryl sulfate | g/l | 0.2 |
| Saccharin | g/l | 2.0 |
| 2-[N-benzylpyridyl-(2)]-ethanesulfonic acid betaine | g/l | 0.3 |
| pH | | 4.6 |
| Temperature | ° C. | 50–60 |
| Current density | amp/dm$^2$ | 1–7 |
| B | | |
| Nickel sulfate . 7H$_2$O | g/l | 310 |
| Nickel chloride . 6H$_2$O | g/l | 50 |
| Boric Acid | g/l | 40 |
| Lauryl sulfate | g/l | 0.2 |
| Saccharin sodium | g/l | 1.0 |
| 1,3,6-naphthalene trisulfonic acid solid salt | g/l | 1.0 |
| 2-[N-benzylpyridyl-(4)]-ethanesulfonic acid betaine | g/l | 0.3 |
| pH | | 4.6 |
| Temperature | ° C. | 50–60 |
| Current density | amp/dm$^2$ | 1–7 |
| C | | |
| Nickel sulfate . 7H$_2$O | g/l | 280 |
| Nickel chloride . 6H$_2$O | g/l | 40 |
| Boric Acid | g/l | 40 |
| Lauryl sulfate | g/l | 0.2 |
| Dibenylsulfonimide | g/l | 8.0 |
| Propargyl alcohol | g/l | 0.04 |
| 1,2-bis-[2-(2-sulfoethyl)-pyridinium(1)-methyl]-benzene | g/l | 0.15 |
| pH | | 4.6 |
| Temperature | ° C. | 50–60 |
| Current density | amp/dm$^2$ | 1–7 |

EXAMPLE X

A. The procedure of Example III-A is followed except that 18 g (0.2 mole) of methallyl chloride is substituted for the o-methylbenzyl chloride used therein to yield, as the final product, 2-[N-(2-methylpropen-2-yl)-pyridyl-(2)]-ethane sulfonic acid betaine, also known as 2-[N-methallyl-pyridyl-(2)]-ethane sulfonic acid betaine, decomposition point: 196° C.

B. 2-[N(2-methylpropen-2-yl)-pyridyl-(4)]-ethane sulfonic acid betaine, also known as 2-[N-methallyl-pyridyl-(4)]-ethane sulfonic acid betaine, decomposition point: 208° C., is obtained in similar fashion by using an equivalent quantity each of 4-pyridyl ethane sulfonic acid sodium salt and methallyl chloride as reactants.

What is claimed is:

1. A pyridyl alkyl sulfonic acid betaine having the formula:

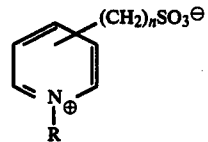

in which the substituent —(CH$_2$)$_n$SO$_3^\ominus$ is in the 2- or 4-position of the pyridyl ring; n is the integer 1 or 2; and R is CH$_2$COOH.

2. 2-[N-carboxymethyl-pyridyl-(2)]-ethanesulfonic acid betaine.

3. 2-[N-carboxymethyl-pyridyl-(4)]-ethanesulfonic acid betaine.

4. [N-carboxymethy-pyridyl-(4)]-methanesulfonic acid betaine.

* * * * *